United States Patent [19]

Sakashita et al.

[11] Patent Number: 4,985,516
[45] Date of Patent: Jan. 15, 1991

[54] CURABLE COMPOSITION

[75] Inventors: Takeshi Sakashita; Masami Arata, both of Iwakuni; Takashi Yamamoto, Wagi, all of Japan

[73] Assignee: Mitsui Petrochemical Industries, Ltd., Tokyo, Japan

[21] Appl. No.: 418,975

[22] Filed: Oct. 10, 1989

Related U.S. Application Data

[63] Continuation of Ser. No. 109,035, Oct. 16, 1987, abandoned.

[30] Foreign Application Priority Data

Oct. 30, 1986 [JP] Japan ............................ 256797/86
Oct. 30, 1986 [JP] Japan ............................ 256798/86
Dec. 26, 1986 [JP] Japan ................................. 308541

[51] Int. Cl.$^5$ ...................... C08F 4/52; C08F 222/16
[52] U.S. Cl. .................................................. 526/196
[58] Field of Search ........................................ 526/196

[56] References Cited

U.S. PATENT DOCUMENTS

| | | | |
|---|---|---|---|
| 3,051,689 | 8/1962 | Zutty | 526/196 |
| 3,112,298 | 11/1963 | Welch | 526/196 |
| 3,116,271 | 12/1963 | Watt et al. | 526/196 |
| 3,127,380 | 3/1964 | Welch | 526/196 |
| 3,238,186 | 3/1966 | Schultz et al. | 526/196 |
| 4,182,035 | 1/1980 | Yamauchi et al. | 523/116 |
| 4,385,153 | 5/1983 | Ritter | 526/196 |
| 4,626,310 | 12/1986 | Ritter | 526/196 |
| 4,639,498 | 1/1987 | Ritter | 526/196 |
| 4,731,425 | 3/1988 | Ritter | 526/196 |

FOREIGN PATENT DOCUMENTS 2000789  1/1979  United Kingdom ............... 526/196

Primary Examiner—Joseph L. Schofer
Assistant Examiner—N. Sarofim
Attorney, Agent, or Firm—Nixon & Vanderhye

[57] ABSTRACT

A curable composition effective for use for dental adhesive and exhibiting superior water-resistant bonding performance and high bonding strength onto enamel, dentine and dental alloys without imparting to dental pulp any irritative influence, which composition comprises (A) a monofunctional monomer based on (meth)acrylate,
(B) a polyfunctional monomer based on (meth)acrylate,
(C) an acidic group-containing monomer based on (meth)acrylate having in the moleucle at least one (meth)acryloyloxyl group and
(D) a trialkylboron or its oxide.

4 Claims, No Drawings

CURABLE COMPOSITION

CROSS-REFERENCE TO RELATED APPLICATIONS

This application is a continuation of earlier application Ser. No. 07/109,035 filed Oct. 16, 1987, now abandoned.

BACKGROUND OF THE INVENTION

1. Field of the Invention

The present invention relates to a curable composition and more particularly to a curable composition effective for an adhesive for dental use which is superior in the water-resistant bonding and in the low temperature curing performance at around ordianary temperature and which exhibits a superior bonding performance for natural materials of teeth, such as, enamel and dentine, as well as for dental alloys, without imparting to the dental pulp any defective influence, such as irritation.

2. Description of the Prior Art

Hitherto, there have been proposed many adhesive compositions for orthodontic and corrective treatments of human teeth, composed of a monomer polymerizable by radical polymerization, such as, a vinyl monomer based on (meth)acrylate and so on, and of a catalyst. For example, a curable composition composed of a vinyl monomer based on (meth)acrylate, an aromatic carboxylic acid (anhydride) containing (meth)acryloyloxy group, an amine and a sulfinic acid (salt), as disclosed in the Japanese patent application Laid-Open No. 44508/1985; an adhesive composition consisting of an ester of (meth)acrylic acid exsisting at ordinary temperature as liquid, an amine, a sulfinic acid (salt) and a peroxide, as decribed in the Japanese patent application Laid-Open No. 39331/1978; and an adhesive composition consisting of MMA, 4-META and tributyl borane, as reported in the magazine "The Japanese Journal of Conservative Dentistry" 28, 452–478, (1985) may be of typical.

However, it had been very difficult to attain sufficient adhesion onto the natural human teeth, especially onto the dentine treated with a mild etching agent, such as, EDTA or the like, using the curable compositions and adhesives of prior art.

SUMMARY OF THE INVENTION

An object of the invention is to provide a curable composition in which the defects of the prior art compositions have eliminated.

Another object of the present invention is to provide a curable composition excellent in the low temperature curability at around the ordinary temperature and in the water-resistant bonding performance.

A further object of the present invention is to provide a curable composition exhibiting a superior adhesion onto enamel, dentine and verious dental alloys, in particular, onto the materials of teeth, such as, dentine etc.

A still further object of the present invention is to provide a curable composition superior in the use for a dental adhesive in the corrective treatment of human teeth without imparting to the dental pulp any defective influence, such as irritation and so on.

According to the present invention, a curable composition is proposed, which comprises (A) a monofunctional monomer based on (meth)acrylate,
(B) a polyfunctional monomer based on (meth)acrylate,
(C) an acidic group-containing monomer based on (meth)acrylate having in the molecule at least one (meth)acryloyloxyl group and
(D) a trialkylboron or its oxide.

DETAILED DESCRIPTION OF THE INVENTION

The monofunctional monomer (A) based on (meth)acrylate to be employed in the curable composition according to the present invention may contain functional groups other than acidic group.

As the monofunctional monomer (A), there may be enumerated:

($A_1$) hydrocarbyl group-containing (meth)acrylates, such as, methyl (meth)acrylate, ethyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth)acrylate and isobornyl (meth)acrylate;

($A_2$) hydroxyl group-containing (meth)acrylates, such as, 2-hydroxyethyl (meth)acrylate, 2-hydroxypropyl (meth)acrylate and so on;

($A_3$) ethylene glycol unit-containing (meth)acrylates, such as, ethylene glycol monomethyl ether (meth)acrylate, ethylene glycol monoethyl ether (meth)acrylate, ethylene glycol monododecyl ether (meth)acrylate, diethylene glycol monomethyl ether (meth)acrylate, polyethylene glycol monomethyl ether (meth)acrylate, polyethylene glycol monoethyl ether (meth)acrylate and so on;

($A_4$) fluoro substituent group-containing (meth)acrylates, such as, trifluoroethyl(meth)acrylate, perfluorooctyl(meth)acrylate and so on;

($A_5$) silane (meth)acrylates, such as, γ-(meth)acryloyloxypropyl trimethoxy silane, γ-(meth)acryloyloxypropyl tri(trimethylsiloxy) silane and so on; and ($A_6$) tetrahydofurfuryl (meth)acrylate, wherein they may be employed solely or in mixture of two or more of them. Among them, alkyl (meth)acrylates, such as, methyl (meth)acrylate, ethyl (meth)acrylate, hexyl (meth)acrylate and dodecyl (meth)acrylate as well as hydroxyl group-containing (meth)acrylates, such as, 2-hydroxyethyl (meth)acrylate, 2-hydroxypropyl (meth)acrylate and so on are preferable and, especially, methyl methacrylate, n-hexyl methacrylate, 2-hydroxyethyl methacrylate and 2-hydroxypropyl methacrylate are most preferable to use either solely or in mixture of them.

The polyfunctional monomer (B) to be incorporated in the curable composition according to the present invention is a polyfunctional monomer based on (meth)acrylate having in the molecule at least two (meth)acryloyloxyl groups.

Examples therefor include:

($B_1$) poly(meth)acrylates of alkane polyols, such as, ethylene glycol di(meth)acrylate, propylene glycol di(meth)acrylate, butylene glycol di(meth)acrylate, neopentyl glycol di(meth)acrylate, hexylene glycol di-(meth)acrylate, trimethylolpropane tri(meth)acrylate, glycerol tri(meth)acrylate, pentaerythritol tetra(meth)acrylate and so on;

(B₂) poly(meth)acrylates of (poly)oxyalkanepolyols, such as, diethylene glycol di(meth)acrylate, dipropylene glycol di(meth)acrylate, triethylene glycol di(meth)acrylate, tetraethylene glycol di(meth)acrylate, dibutylene glycol di(meth)acrylate, dipentaerythritol hexa(meth)acrylate and so on;

(B₃) epoxy(meth)acrylates, represented by the general formula (I)

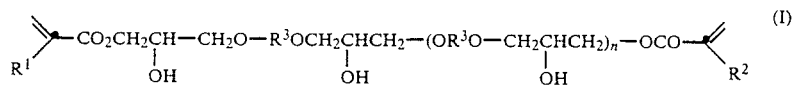

in which $R^1$ and $R^2$ represent each H or $CH_3$, n is zero or a positive integer and $R^3$ denotes a divalent aliphatic, cycloaliphatic or aromatic residue permissible of containing therein an oxygen or sulfur atom;

(B₄) cycloaliphatic or aromatic di(meth)acrylates represented by the general formula (II)

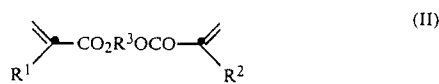

in which $R^1$ and $R^2$ stand each for H or $CH_3$ and $R^3$ denotes a divalent cycloaliphatic or aromatic residue having at least one cyclic group and permissible of containing in this residue an oxygen or sulfur atom; and (B₅) cycloaliphatic di(meth)acrylates expressed by the general formula (III)

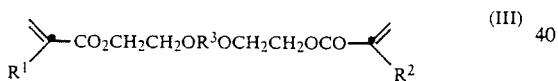

in which $R^1$ and $R^2$ stand each for H or $CH_3$ and $R^3$ denotes a divalent cycloaliphatic residue having at least one cyclic group and permissible of containing in this residue an oxygen or sulfur atom.

Examples of aliphatic, cycloaliphatic and aromatic residue of $R^3$ in the above general formula (I) include:

—(CH₂)₂—, —(CH₂)₄—,

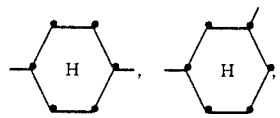

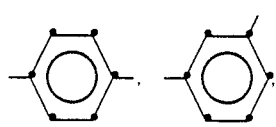

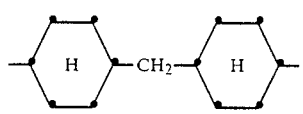

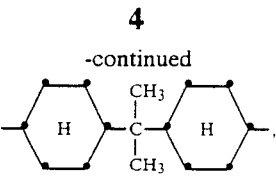

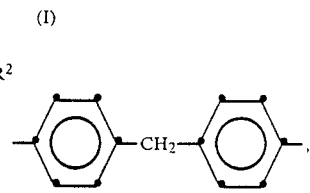

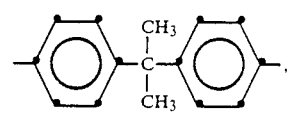

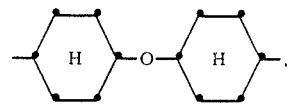

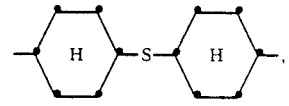

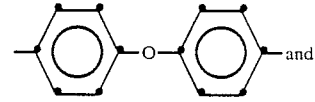

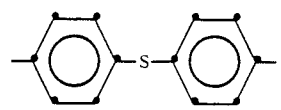

Examples of cycloaliphatic and aromatic residues of $R^3$ in the above general formula (II) include:

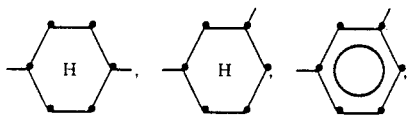

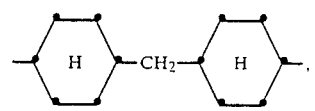

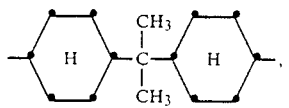

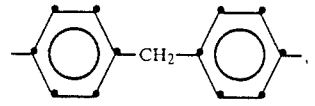

-continued

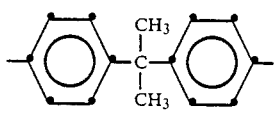

Examples of cycloaliphatic residue of $R^3$ in the above general formula (III) include:

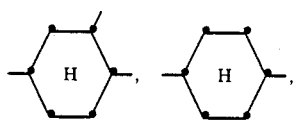

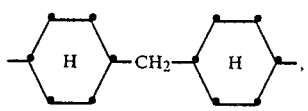

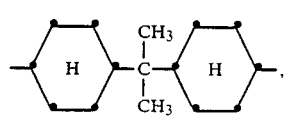

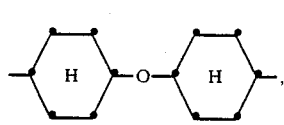

Among the polyfunctional monomers based on (meth)acrylate, poly(meth)acrylates of alkanepolyols, poly(meth)acrylates of (poly)oxyalkanepolyols and epoxy (meth)acrylates may preferably be employed and, in particular, ethylene glycol di(meth)acrylate, neopentyl glycol di(meth)acrylate, diethlene glycol di(meth)acrylate, and compounds represented by the formula

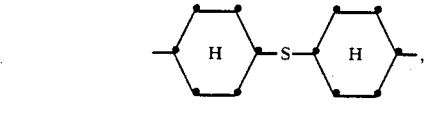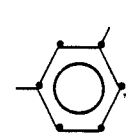

in which $R^1$ and $R^2$ stand each for H or $CH_3$, are preferable for use.

Examples of polyfunctional monomers (B) based on (meth)acrylate may further include: (B₆) polyfunctional monomers based on (meth)acrylate represented by the general formula (IV)

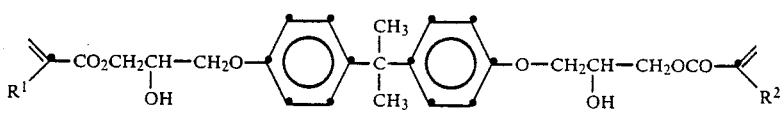

in which $R^1$ and $R^2$ stand each for H or $CH_3$, $R^3$ denotes a divalent aromatic residue having at leat one aromatic ring and permissible of containing in this residue an oxygen or sulfur atom and n and m represent each a positive integer.

As the divalent aromatic residue of $R^3$ of the above general formula (IV), there may be exemplified:

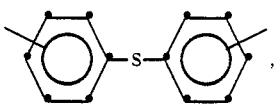

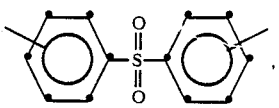

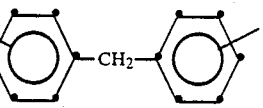

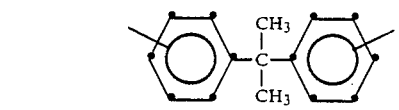

Among them,

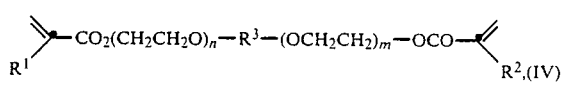

are more preferable for the residue of $R^3$ and, in particular,

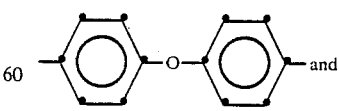 and

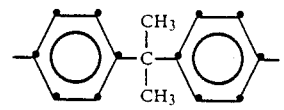

are most preferable.

For the polyfuntional monomers based on (meth)acrylate of above ($B_6$) of the general formula (IV), there may be enumerated:

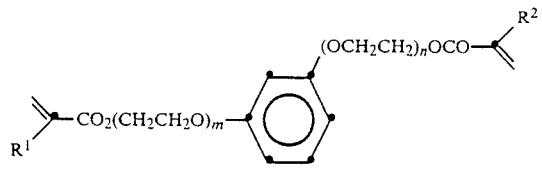

in which $R^1$ and $R^2$ stand each for H or $CH_3$ and $m+n=2-20$;

in which $R^1$ and $R^2$ stand each for H or $CH_3$ and $m+n=2-20$;

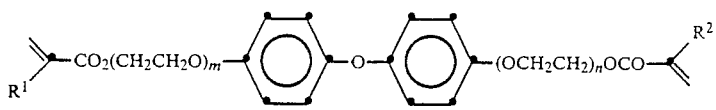

in which $R^1$ and $R^2$ stand each for H or $CH_3$ and $m+n=2-20$;

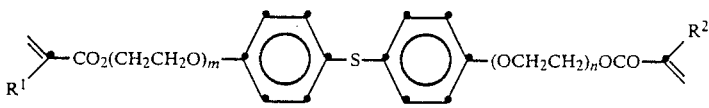

in which $R^1$ and $R^2$ stand each for H or $CH_3$ and $m+n=2-20$;

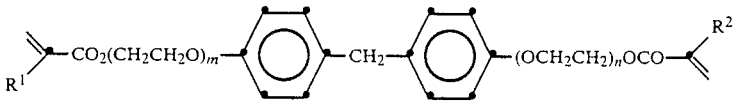

in which $R^1$ and $R^2$ stand each for H or $CH_3$ and $m+n=2-20$; and

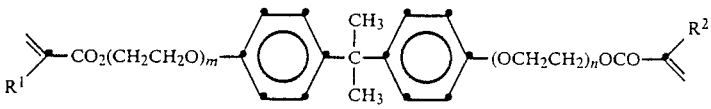

in which $R^1$ and $R^2$ stand each for H or $CH_3$ and $m+n=2-20$; and in particular,

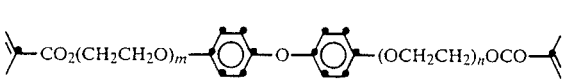

in which $m+n=2-10$ and

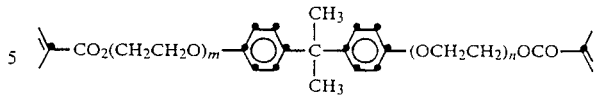

in which $m+n=2-10$ are most preferable.

As the polyfunctional monomer (B) based on (meth)acrylate, moreover, ($B_7$) polyfunctional monomers based on (meth)acrylate having in the molecule at least one urethane linkage may also be employed, for example, adducts of one mole of a diisocyanate compound with two moles of a hydroxyl group-containing (metyh)acrylate, such as, 2-hydroxyethyl (meth)acrylate and so on.

Here, as the diisocyanate compound, aliphatic, cycloaliphatic and aromatic diisocyanate compounds can be employed, such as, hexamethylene diisocyanate, lysine diisocyanate, 2,2(4),4-trimethylhexamethylene diisocyanate, dicyclohexyldimethylmethane-p,p'-diisocyanate, isophorone diisocyanate, tolylene diisocyanate, xylylene diisocyanate, diphenylmethane diisocyanate, naphthalene diisocyanate and so on.

As the concrete examples of polyfunctional monomers of ($B_7$) based on (meth)acrylate having urethane linkage, followings may be enumerated:

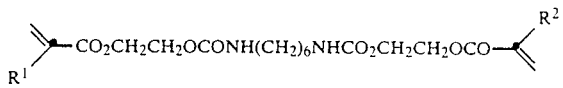

in which $R^1$ and $R^2$ stand each for H or $CH_3$;

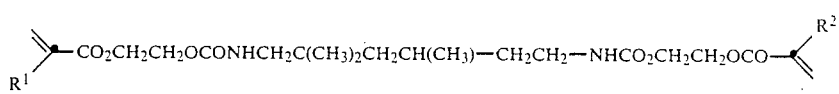

in which $R^1$ and $R^2$ stand each for H or $CH_3$;

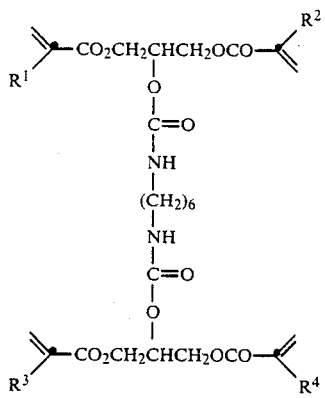

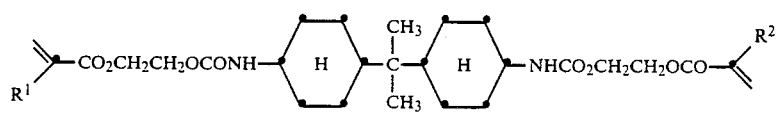

in which $R^1$, $R^2$, $R^3$ and $R^2$ stand each for H or $CH_3$;

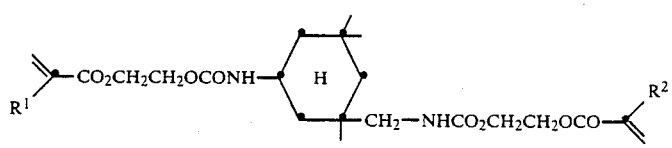

in which $R^1$ and $R^2$ stand each for H or $CH_3$;

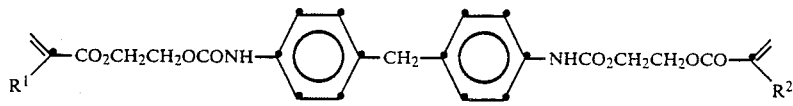

in which $R^1$ and $R^2$ stand each for H or $CH_3$;

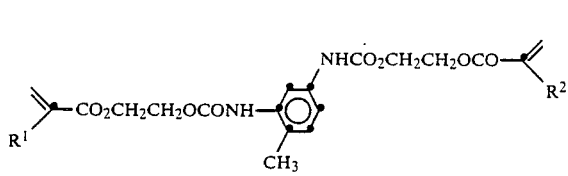

in which $R^1$ and $R^2$ stand each for H or $CH_3$;

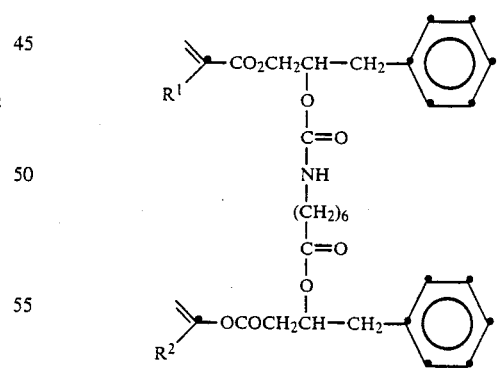

in which $R^1$ and $R^2$ stand each for H or $CH_3$; and in which $R^1$ and $R^2$ stand each for H or $CH_3$.

Among these polyfunctional monomers having urethane linkage based on (meth)acrylate, particularly those of aliphatic and cycloaliphatic ones are preferred and, above all,

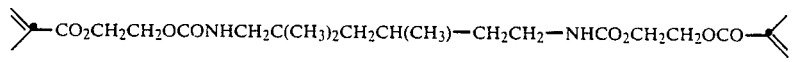

and

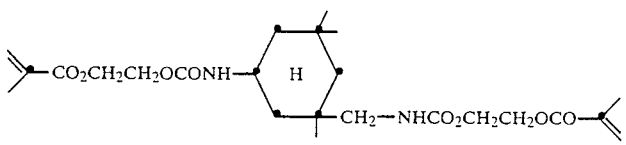

are most preferable.

The polyfunctional monomers (B) based on (meth)acrylate can be used solely or in mixture of two or more of them.

As the acidic group-containing monomer (C) based on (meth)acrylate having in the molecule at least one (meth)acryloyloxyl group to be employed in the curable composition according to the present invention, there may be exemplified:

(C₁) aromatic polycarboxylic acids and anhydride thereof having in the molecule at least one (meth)acryloyloxyl group and (C₂) partial esters of phosphoric acid, such as mono- and diesters and mixtures of these; esters of sulfonic acid and so on, each having at least one (meth)acryloyloxyl group in the molecule.

Concrete examples for the aromatic polycarboxylic acid or anhydride thereof (C₁) having in the molecule at least one (meth)acryloyloxyl group include those which have a molecular structure, in which at least one hydroxyl group of an alkane polyol having in the molecule at least two hydroxyl groups and being permissible of containing oxygen atom is esterified with (meth)acrylic acid and at least one other hydroxyl group thereof is esterified with one carboxyl group of an aromatic polycarboxylic acid having at least three carboxyl groups. An aromatic polycarboxylic acid having at least three carboxyl groups in which at least two carboxyl groups are conbined to neighboring carbon atoms in the aromatic nucleous is preferable, for example, hemimellitic acid, trimellitic acid, prehnitic acid, mellophanic acid, pyromellitic acid or so on.

Examples of the aromatic polycarboxylic acid having (meth)acryloyloxyl group include 4-(meth)acryloyloxymethoxycarbonyl phthalic acid and its anhydride, 4-(meth)acryloyloxybutoxycarbonyl phthalic acid and its anhydride, 4-(meth)acryloyloxybutoxycarbonyl phthalic acid and its anhydride, compounds represented by the formulae

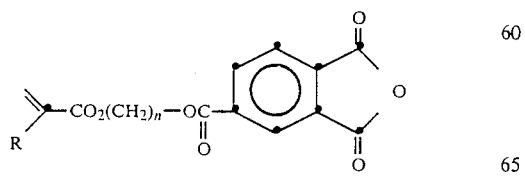

in which n is an integer of 6–12 and R stands for H or $CH_3$,

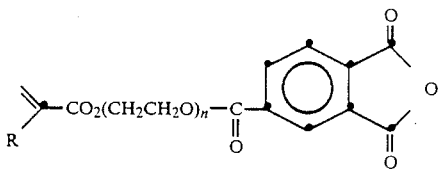

in which n is an integer of 2–50 and R stands for H or $CH_3$, and

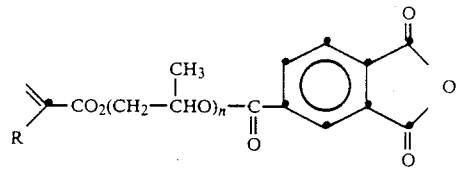

in which n is an integer of 1–50 and R stands for H or $CH_3$; and further 4-[2-hydroxy-3-(meth)acryloyloxypropoxycarbonyl] phthalic acid and its anhydride, 2,3-bis(3,4-dicarboxybenzoyloxy)propyl (meth)acrylate and its anhydride, 2-(3,4-dicarboxybenzoyloxy)-1,3-dimethacryloyloxy propane and anhydride thereof.

Concrete examples of the compound (C₂) of partial ester of phosphoric acid, namely mono- and diester of phosphoric and mixture of them, or sulfonate, namely an ester of sulfonic acid, each having in the molecule at least one (meth)acryloyloxyl group include 2-(meth)acryloyloxyethylphenyl acid phosphate, bis-[2-(meth)acryloyloxyethyl] acid phosphate, bis-[3-(meth)acryloyloxypropyl] acid phosphate, 2-(meth)acryloyloxyethyl-phenylphosphonate, compounds represented by the formulae

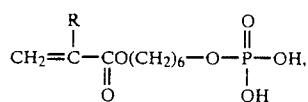

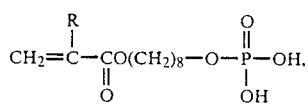

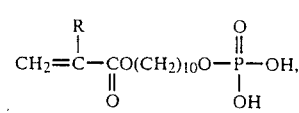

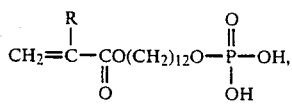

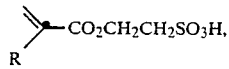

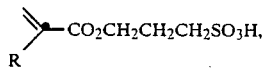

The acid group-containing monomers (C₁) based on (meth)acrylate and each having in the molecule at least one (meth)acryloyloxyl group also can be employed solely or in mixture of two or more of them. Among them, aromatic polycarboxylic acids and their anhydrides (C₁) having in the molecule at least one acryloyloxy group are preferred and, in particular, 4-(meth)acryloyloxyethoxycarbonyl phthalic acid and its anhydride are most preferable. Particularly, the use of 4-methacryloyloxyethoxycarbonyl phthalic acid anhydride improves the adhesion onto teeth and the durability in aqueous media.

Concrete examples of the trialkylboron and the oxydation product thereof (D) to be employed in the curable composition according to the present invention include triethylboron, tripropylboron, triisopropylboron tri-n-butylboron, tri-n-amylboron, triisoamylboron and tri-sec-amylboron and oxidation product of these trialkylboron, in which these compounds are partly oxydized. The trialkylboron or oxidation product thereof (D) can also be employed solely or in a mixture of two or more of them. Among these, tri-n-butylborn and the partial oxidation product thereof are preferable.

While there is no special restriction as to the mixing proportion of the monofunctional monomer (A) based on (meth)acrylate and the polyfunctional monomer (B) based on (meth)acrylate, it is preferable in general to employ a formulation consisting of 5-95% by weight of the monofunctional monomer (A) based on (meth)acrylate and 95-5% by weight of polyfunctional monomer (B) based on (meth)acrylate, in particular, a formulation consisting of 10-95% by weight of monofunctional monomer (A) and 90-5% by weight of polyfunctional monomer (B) and, most preferably, a formulation consisting of 25-90% by weight of the monofunctional monomer (A) and 75-10% by weight of polyfunctional monomer (B). Within the range as given above, the curable composition according to the present invention will exhibit a superior adhesion onto the dentine and excellent durability in aqueous media and, in particular, high bonding strength and high water-fastness will be attained even when an etching treatment of dentine with a mild acid, such as EDTA.

The amount of the acidic group-containing monomer (C) based on (meth)acrylate to be incorporated in the curable composition according to the present invention may, in general, be in the range from 1 to 50 parts by weight, preferably from 3 to 30 parts by weight, especially from 5 to 15 parts by weight, based on 100 parts by weight of the monofunctional monomer (A) and the polyfunctional monomer (B).

The amount of trialkylboron or its partial oxidation product (D) to be incorporated in the curable composition according to the present invention may, in general, be in the range from 2 to 100 parts by weight, preferably from 5 to 70 parts by weight and, most preferably, from 5 to 50 parts by weight, based on 100 parts by weight of the sum of the monofunctional monomer (A), the polyfunctional monomer (B) and the acidic group-containing monomer (C). For the practical use of the composition according to the present invention, the trialkylboron or its oxidation product (D) is admixed to a premix of the monomers (A), (B) and (C) of the composition from a separately reserved stock directly before the practical application, since the polymerization reaction will start within a period of from several seconds to several tens minutes after the admixing to the premix.

The curable composition according to the present invention may include beside the above described essential components other additives, for example, powdery inorganic filler, organic polymer substances, polymerization retarder and so on. Example of the pulverous inorganic filler are kaolin, talc, clay, calcium carbonate, silica powder, powdered silica-alumina, pulverous alumina, titanium oxide, calcium phosphate, pulverized glass, quartz powder and so on. Examples of organic polymer substance include waxes, copolymer of ethylene/vinyl acetate, polymethyl acrylate, polymethyl methacrylate, copolymers of these and so on. These additives may be incorporated in an adequate amount.

The curable composition according to the present invention exhibits superior low temperature curing and excellent water-resistant bonding performance together with superior adhesion onto teeth materials, such as enamel and dentine without causing any irritation to the dental pulp, so that it can be used for various applications, such as, for bonding agent, for composite resins and hard resins for dental uses and as composite resinous mass for accuracy work in various fields other than dental uses. An application for bonding agent for the composite resin in dental use may be most preferable.

DETAILED DESCRIPTION OF PREFERRED EMBODIMENTS

In the following, the present invention will further be described concretely by way of Examples.

Also Application Examples of the composition for preparation of light-curable dental composite resin and dental filling mass are given.

In the Examples and Comparison Examples, compounds used are denoted by each specific abbreviation as recited below:

MMA: Methyl methacrylate
HMA: n-Hexyl methacrylate
HEMA: 2-Hydroxyethyl methacrylate
HPMA: 2-Hydroxypropyl methacrylate
NPG: Neopentyl glycol dimethacrylate
2G: Diethylene glycol dimethacrylate
PMMA: Polymethyl methacrylate
BIS-GMA:

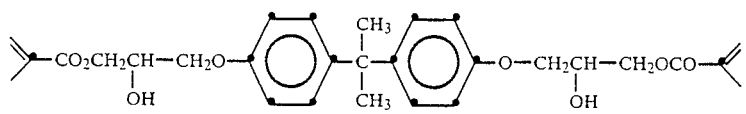

DPEMA:

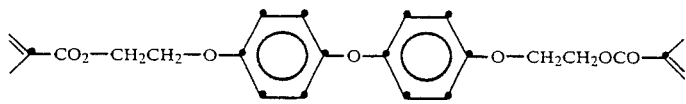

2,6E:

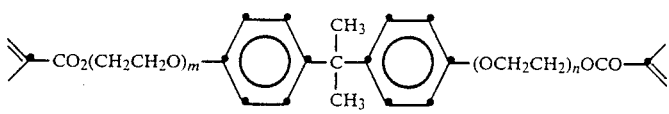

in which m+n=2.6 (average),
RDMA:

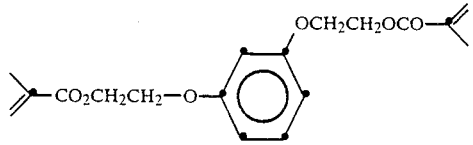

UDMA:

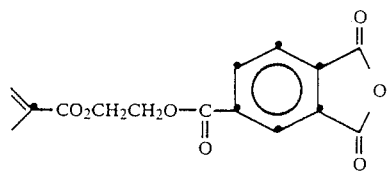

4-MET:

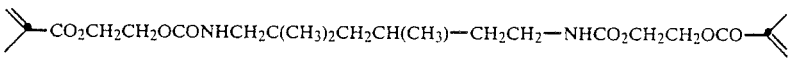

GUMM:

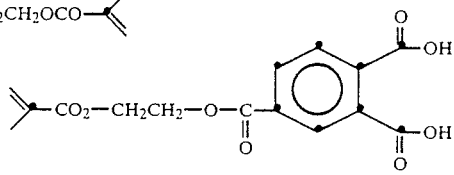

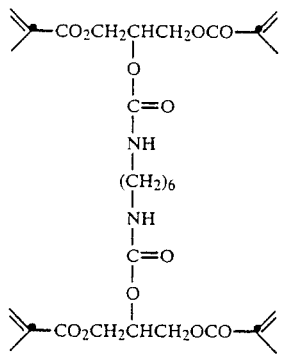

HEIP:

TBB.O: A partial oxidation product of tri-n-butylboron
BPO: Benzoyl peroxide
DEPT: Diethanol-p-toluidine
PTSNa: Sodium paratoluenesulfinate
HQME: Hydroquinone monomethyl ether For evaluating the bonding strength of the compositions tested, the following procedures were employed:

A front tooth of a cattle was polished on its enamel face or its dentine face with a #600 emery paper to smooth the surface. The tooth was then subjected to an etching treatment with 65% by weight aqueous solution of phosphoric acid for 30 seconds for the enamel and

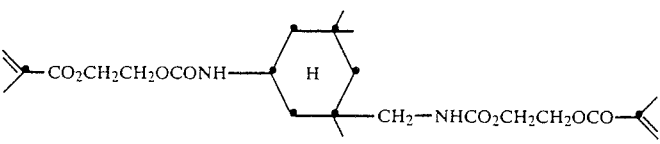

4-META:

with 0.3M aqueous EDTA.2Na—0.2M aqueous EDTA.Fe.Na (pH7.4) for 60 seconds for the dentine. After a sufficient water wash, the etched surface was dried by blowing air. Then a sheet of cellophane tape (about 13 mm × 13 mm) having a circular cut off of a dismeter of 5 mm was sticked thereon. A bonding agent for use for each Example or Comparison Example was coated on the exposed tooth surface in the cut off of the tape and the coated layer was blown briefly with air. On the other hand, a cylindrical Teflon (trademark) mold having a mold recess with a diameter of 5 mm and a depth of 2 mm as corresponding to the cut off circle of the tape was charged with a light-curable dental composite resin as explained afterwards and the so charged layer was covered by a cellophane paper. The resin layer was then irradiated through the cellophane paper by a visible light using a visible light projector Translux (trademark of the firm Kulzer) for 30 seconds to harden the composite resin. Then, an acryl resin rod was bonded onto the so hardened surface of the composite resin with an adhesive Super-Bond C&B (trademark, a product of the firm Sun Medical) to prepare a test piece for testing bonding strength. After storage for 30 minutes at room temperature, the test piece was immersed in water at 37° C. for 24 hours and then taken out and kept in air at 23° C. for 10 minutes, before it was subjected to a tensile test at 23° C. at a rate of 2 mm/min. The rupture face of the test piece after the tensile test was found as consisting of either the material of the sample tooth, material of composite resin resulting from an aggregation rupture or interface between the composite resin layer and dentine layer.

PREPARATION EXAMPLE I

Preparation of a Light-Curable Composite Resin

In a two-roll kneader, 7.5 g of triethylene glycol dimethacrylate, 7.5 g of 1,3-bis-(methacryloxyethoxy)-benzene, 15 g of an adduct of one mole of 2,2,4-trimethyl hexamethylenediamine diisocyanate with 2 moles of 2-hydroxyethyl methacrylate, 40 g of composite filler powder synthesized by the method explained afterwards, 30 g of Micropowder Silica RM-50 (fine powder silica product of the firm Nippon Aerosil K.K.) and 4 mg of hydroquinone monomethyl ether were kneaded to prepare a mixture. 10 g of this mixture were mixed with 45 mg of camphorquinone and 45 mg of 4-diethylaminobezoic acid using a spatula sufficiently to prepare a light-curable composition.

PREPARATION EXAMPLE II

Preparation of Composite Filler Powder 0.1 g of benzoyl peroxide was dissolved in 10 g of trimethacrylate of trimethylolpropane and the solution was placed in an agate mortar and thereto was admixed fine pulverous silica Aerosil R972 (trademark of Nippon Aerosil K.K., average particle size of 16 mμ) in small portions. The consistency increased gradually until a state of a sticky aggregated powdery mass is obtained. The resulting mixture was transferred in a small rubber roll kneader and thereto was further added powdery silica in portions in an amount of total of 9.5 g. The so obtained paste was taken out of the roll kneader and was molded on a press at a temperature of 120° C. under a pressure of 150–200 Kg/cm² for 10 minutes to effect heat curing thereof. The hardened product was crushed in a ball mill and was then sieved. 18.0 g of composite filler powder of an undersize of 230-mesh were obtained. The average particle size of this powder was 11μ.

EXAMPLE 1

6 g of MMA, 3 g of NPG, 1 g of 4-META, namely 4-methacryloxyethoxycarbonyl phthalic anhydride, and 2 mg of HQME were mixed together at room temperature to prepare a liquid monomer mixture (A). To 2 parts by weight of this liquid mixture, there was admixed 1 part by weight of TBB.O (a partial oxidation product of tri-n-butylboron marketed from the firm Sun Medical) to prepare a curable composition. This mixture was coated on a test sample of cattle tooth using a painting brush in a thin coating layer, whereupon a test piece for testing the bonding strength as described above was prepared by the procedures described previously. The results are summarized in Table 1.

EXAMPLES 2–8, COMPARISON EXAMPLE 1 and COMPARISON EXAMPLES 3–4

A liquid monomer mixture (A) was prepared as in Example 1 using the monomer components in amounts as given in Table 1. By mixing the liquid mixture (A) with TBB.O (product of Sun Medical) in the proportion given in Table 1, each curable test composition was prepared. Using this curable composition, the test piece for testing the bonding strength was prepared in the manner as given in Example 1. Results are summarized also in Table 1.

COMPARISON EXAMPLE 2

Using 100 parts by weight of MMA, 11 parts by weight of 4-META, 80 parts by weight of PMMA (for Super-Bond C&B of Sun Medical) and 2 mg of hydroquinone monomethyl ether, a liquid monomer mixture (A) was prepared. By mixing this liquid mixture (A) with TBB.O in a proportion as given in Table 1, a curable composition was prepared. The preparation of test piece was effected in the manner as given in Comparison Example 1. Results are summarized also in Table 1.

COMPARISON EXAMPLE 5

6 g of MMA, 3 g of NPG, 1 g of 4-META, 0.2 g of BPO and 2 mg of HQME were mixed at room temperature to prepare a liquid monomer mixture (A). On the other hand, another liquid mixture was prepared from 0.1 g of DEPT, 0.4 g of PTSNa and 9.5 g of 99% ethanol. By mixing the above liquid mixtures (A) and (B) in equal amount, a cuarable composition was obtained. This composition was coated on the sample tooth using a painting brush. The preparation of test piece for testing the bonding strength was effected in the manner as given in Example 1. Results are summarized also in Table 1.

TABLE 1

| Example or Comparison Example | Monomer composition and proportion | | | | Bonding Strength (Kg/cm²) | |
|---|---|---|---|---|---|---|
| | Compt.(A)[1] [Weight ratio] | Compt.(B)[2] [B/(A+B) in wt. %] | Compt.(C)[3] [C/(A+B) in wt. %] | Compt.(D)[4] [D/(A+B+C) in wt. %] | to enamel[5] | to dentine[6] |
| Example 1 | MMA — | NPG 33 | 4-META 11 | TBB-O 33 | 180 | 72 |

TABLE 1-continued

| Example or Comparison Example | Monomer composition and proportion | | | | Bonding Strength (Kg/cm²) | |
|---|---|---|---|---|---|---|
| | Compt.(A)[1] [Weight ratio] | Compt.(B)[2] [B/(A+B) in wt. %] | Compt.(C)[3] [C/(A+B) in wt. %] | Compt.(D)[4] [D/(A+B+C) in wt. %] | to enamel[5] | to dentine[6] |
| Example 2 | MMA | BIS-GMA 33 | 4-META 11 | TBB-O 33 | 170 | 70 |
| Example 3 | MMA | 2G 33 | 4-META 11 | TBB-O 33 | 180 | 80 |
| Example 4 | MMA/HEMA 85/15 | NPG 33 | 4-MET 11 | TBB-O 33 | 175 | 75 |
| Example 5 | MMA/HMA 50/50 | BIS-GMA 33 | 4-META 11 | TBB-O 33 | 175 | 72 |
| Example 6 | MMA/HPMA 85/15 | 2G 33 | 4-META 11 | TBB-O 25 | 190 | 85 |
| Example 7 | MMA/HEMA 85/15 | 2G 45 | 4-META 11 | TBB-O 20 | 191 | 88 |
| Example 8 | MMA/HPMA 60/40 | 2G 45 | 4-META 15 | TBB-O 20 | 188 | 85 |
| Compar. Ex. 1 | MMA | — | 4-META 11 | TBB-O 33 | 105 | 20 |
| Compar. Ex. 2 | MMA[7] | — | 4-META 11 | TBB-O 20 | 150 | 53 |
| Compar. Ex. 3 | MMA | NPG 33 | — | TBB-O 33 | 135 | 15 |
| Compar. Ex. 4 | — | NPG 100 | 4-META 11 | TBB-O 20 | 130 | 10 gelled |
| Compar. Ex. 5 | MMA | NPG 33 | 4-META 11 | BPO/DEPT/ PTSNa 1.0.5/2 | 150 | 31 |

[1]Monofunctional monomer (A)
[2]Polyfunctional monomer (B)
[3]Acidic group-containing monomer (C)
[4]Partial oxidation product of trialkylboron
[5]For enamel, after immersion in water at 37° C. for 24 hours
[6]For dentine, after immersion in water at 37° C. for 24 hours
[7]Containing 80 parts by weight of PMMA per 100 parts by weight of MMA

EXAMPLE 9

8 g of MMA, 1 g of RDMA, namely 1,3-bis-(methacryloxyethoxy) benzen, 1 g of 4-META, 0.1 g of PMMA and 2 mg of HQME were mixed at room temperature to prepare a liquid monomer mixture (A). To 2 parts by weight of this liquid mixture, there was admixed 1 part by weight of TBB.O to prepare a curable composition. This mixture was coated on the test sample of cattle tooth using a painting brush, whereupon a test piece for testing the bonding strength as described previously was prepared by the procedures set forth previously. The results are summarized in Table 2.

EXAMPLES 10-12 and COMPARISON EXAMPLES 6-7

A test piece for testing the bonding strength was prepared in the manner as given in Example 9, except that monomer compositions given in Table 2 were used instead of using those of Example 9. Results are summarized also in Table 2.

EXAMPLE 13-16 and COMPARISON EXAMPLE 8

A liquid monomer mixture (A) was prepared as in Example 9 using the monomer components of Table 2 in amounts as given therein. By mixing the liquid mixture (A) with TBB.O in the proportion given in Table 2, each curable test composition was prepared. Using this curable composition, the test piece for testing bonding strength was prepared in the manner as given in Example 9. Results are summarized also in Table 2.

COMPARISON EXAMPLE 9

2.7 g of HEMA, 6.3 g of 2,6E, 1 g of 4-META, 0.1 g of BPO and 2 mg of HQME were mixed at room temperature to prepare a liquid monomer mixture (A). On the other hand, a liquid mixture (B) was prepared from 0.05 g of DEPT, 0.2 g of PTSNa and 9.75 g of 99% ethanol. By mixing the above liquid mixtures (A) and (B) in equal amount, a cuarable composition was obtained. This composition was coated on the sample tooth using a painting brush. The preparation of test piece for testing the bonding strength was effected in the manner as explained previously. Results are summarized also in Table 2.

TABLE 2

| Example or Comparison Example | Monomer composition and proportion | | | | Bonding Strength (Kg/cm²) | |
|---|---|---|---|---|---|---|
| | Compt.(A)[1] [Weight ratio] | Compt.(B)[2] [B/(A+B) in wt. %] | Compt.(C)[3] [C/(A+B) in wt. %] | Compt.(D)[4] [D/(A+B+C) in wt. %] | to enamel[5] | to dentine[6] |
| Example 9 | MMA | RDMA 11 | 4-META 11 | TBB-O 33 | 175 | 90 |
| Example 10 | MMA | DPEMA 11 | 4-META 11 | TBB-O 33 | 190 | 110 |
| Example 11 | MMA | 2,6E | 4-META | TBB-O | 195 | 105 |

TABLE 2-continued

| Example or Comparison Example | Compt.(A)[1] [Weight ratio] | Compt.(B)[2] [B/(A+B) in wt. %] | Compt.(C)[3] [C/(A+B) in wt. %] | Compt.(D)[4] [D/(A+B+C) in wt. %] | Bonding Strength (Kg/cm²) to enamel[5] | to dentine[6] |
|---|---|---|---|---|---|---|
| 11 | — | 11 | 11 | 33 | | |
| Example 12 | MMA/HMA 90/10 | DPEMA 11 | 4-MET 11 | TBB-O 33 | 191 | 115 |
| Example 13 | MMA/HEMA 50/50 | 2,6E 40 | 4-META 11 | TBB-O 33 | 192 | 110 |
| Example 14 | HEMA — | 2,6E 70 | 4-META 11 | TBB-O 25 | 205 | 130 |
| Example 15 | HMA — | 2,6E 70 | 4-META 11 | TBB-O 25 | 194 | 125 |
| Example 16 | MMA/HPMA 20/80 | 2,6E 45 | 4-META 15 | TBB-O 20 | 188 | 130 |
| Compar. Ex. 6 | MMA — | — | 4-META 11 | TBB-O 33 | 145 | 60 |
| Compar. Ex. 7 | MMA — | 2,6E 11 | — | TBB-O 33 | 140 | 20 |
| Compar. Ex. 8 | — | 2,6E 100 | 4-META 11 | TBB-O 20 | 160 | 70 |
| Compar. Ex. 9 | HEMA — | 2,6E 70 | 4-META 11 | BPO/DEPT/ PTSNa 1/0.5/2 | 165 | 40 |

[1]Monofunctional monomer (A)
[2]Polyfunctional monomer (B)
[3]Acidic group-containing monomer (C)
[4]Partial oxidation product of trialkylboron
[5]For enamel, after immersion in water at 37° C. for 24 hours
[6]For dentine, after immersion in water at 37° C. for 24 hours

EXAMPLE 17

8 g of MMA, 1 g of UDMA, 1 g of 4-META, 0.1 g of PMMA and 2 mg of HQME were mixed at room temperature to prepare a liquid monomer mixture (A). To 2 parts by weight of this liquid mixture, there was admixed 1 part by weight of TBB.O to prepare a curable composition. This mixture was coated on the test sample of cattle tooth using a painting brush, whereupon a test piece for testing the bonding strength as described previously was prepared by the procedures set forth previously. The results are summarized in Table 3.

EXAMPLES 18-20 AND COMPARISON EXAMPLE 10

A test piece for testing bonding strength was prepared in the manner as given in Example 17, except that monomer compositions given in Table 3 were used instead of using those of Example 17. Results are summarized also in Table 3.

EXAMPLES 21-24 AND COMPARISON EXAMPLE 11

A liquid monomer mixture (A) was prepared as in Example 17 using the monomer components of Table 3 in amounts as given therein. By mixing the liquid mixture (A) with TBB.O in the proportion given in Table 3, each curable test composition was prepared. Using this composition, the test piece for testing the bonding strength was prepared. Results are summarized also in Table 3.

COMPARISON EXAMPLE 12

2.7 g of HEMA, 6.3 g of HEIP, 1 g of 4-META, 0.1 g of BPO and 2 mg of HQME were mixed at room temperature to prepare a liquid monomer mixture (A). On the other hand, a liquid mixture (B) was prepared from 0.05 g of DEPT, 0.2 g of PTSNa and 9.75 g of 99% ethanol. By mixing the above liquid mixtures (A) and (B) in equal amount, a cuarable composition was obtained. This composition was coated on the sample tooth using a painting brush and the coating layer was then blown by air briefly to evaporate off ethanol. The preparation of test piece for testing the bonding strength was effected in the manner as explained previously. Results are summarized also in Table 3.

TABLE 3

| Example or Comparison Example | Compt.(A)[1] [Weight ratio] | Compt.(B)[2] [B/(A+B) in wt. %] | Compt.(C)[3] [C/(A+B) in wt. %] | Compt.(D)[4] [D/(A+B+C) in wt. %] | Bonding Strength (Kg/cm²) to enamel[5] | to dentine[6] |
|---|---|---|---|---|---|---|
| Example 17 | MMA — | UDMA 11 | 4-META 11 | TBB-O 33 | 171 | 95 |
| Example 18 | MMA — | GUMM 11 | 4-META 11 | TBB-O 33 | 168 | 90 |
| Example 19 | MMA — | HEIP 11 | 4-META 11 | TBB-O 33 | 190 | 115 |
| Example 20 | MMA/HMA 90/10 | HEIP 11 | 4-MET 11 | TBB-O 33 | 193 | 108 |
| Example 21 | MMA/HEMA 50/50 | HEIP 40 | 4-META 11 | TBB-O 33 | 198 | 121 |

TABLE 3-continued

| Example or Comparison Example | Monomer composition and proportion | | | | Bonding Strength (Kg/cm$^2$) | |
|---|---|---|---|---|---|---|
| | Compt.(A)[1] [Weight ratio] | Compt.(B)[2] [B/(A+B)] in wt. %] | Compt.(C)[3] [C/(A+B)] in wt. %] | Compt.(D)[4] [D/(A+B+C)] in wt. %] | to enamel[5] | to dentine[6] |
| Example 22 | HEMA — | HEIP 70 | 4-META 11 | TBB-O 25 | 203 | 128 |
| Example 23 | HMA — | UDMA 70 | 4-META 11 | TBB-O 20 | 175 | 105 |
| Example 24 | MMA/HPMA 20/80 | UDMA 45 | 4-META 15 | TBB-O 20 | 195 | 120 |
| Compar. Ex. 10 | MMA — | HEIP 11 | — | TBB-O 33 | 138 | 25 |
| Compar. Ex. 11 | — | HEIP 100 | 4-META 11 | TBB-O 20 | 165 | 80 |
| Compar. Ex. 12 | HEMA — | HEIP 70 | 4-META 11 | BPO/DEPT/PTSNa 1/0.5/2 | 163 | 43 |

[1]Monofunctional monomer (A)
[2]Polyfunctional monomer (B)
[3]Acidic group-containing monomer (C)
[4]Partial oxidation product of trialkylboron
[5]For enamel, after immersion in water at 37° C. for 24 hours
[6]For dentine, after immersion in water at 37° C. for 24 hour

What is claimed is:

1. A curable composition consisting essentially of:
(A) a monofunctional monomer based upon (meth)acrylate, in an amount of 5 to 95% by weight;
(B) a polyfunctional monomer based on (meth)acrylate in an amount of 95 to 5% by weight and said (meth)acrylate consists of one or more monomers selected from the group consisting of
($B_1$) poly(meth)acrylates of alkane polyols,
($B_2$) poly(meth)acrylates of (poly)oxyalkanepolyols.
($B_3$) epoxy(meth)acrylates represented by the general formula (I)

$$R^1\!\!>\!\!-CO_2-CH_2\underset{OH}{CHCH_2}O-R^3-OCH_2\underset{OH}{CHCH_2}-$$
$$-(O-R^3-OCH_2\underset{OH}{CHCH_2})_n-OCO-\!\!<\!R_2 \quad (I)$$

in which $R_1$ and $R_2$ represent each H or $CH^3$ n is zero or a positive integer and $R^3$ denotes a divalent aliphatic, cycloaliphatic or aromatic residue permissible or containing therein an oxygen or sulfur atom, ($B_4$) cycloaliphatic or aromatic di(meth)acrylates represented by the general formula (II)

$$R^1\!\!>\!\!-CO_2-R^3-OCO-\!\!<\!R^2 \quad (II)$$

in which $R^1$ and $R^2$ stand each for H or $CH_3$ and $R^3$ denotes a divalent cycloaliphatic or aromatic residue having at least one cyclic group and permissible of containing therein an oxygen or sulfur atom and ($B_5$) cycloaliphatic di(meth)acrylates represented by the general formula (III)

$$R^1\!\!>\!\!-CO_2-CH_2CH_2O-R^3-OCH_2CH_2-OCO-\!\!<\!R^2 \quad (III)$$

in which $R^1$ and $R^2$ stand each for H or $CH_3$ and $R^3$ denotes a divalent cycloaliphatic residue having at least one cyclic group and permissible of containing therein an oxygen or sulfur atom, ($B_6$) polyfunctional monomers based on (meth)acrylate represented by the general formula (IV)

$$R^1\!\!>\!\!-CO_2-(CH_2-CH_2O)_n-R^3(OCH_2CH_2)_m-OCO-\!\!<\!R^2 \quad (IV)$$

in which $R^1$ and $R^2$ stand each for H or $CH_3$, $R^3$ denotes a divalent aromatic residue having at least one aromatic ring and being permissible of containing therein an oxygen or sulfur atom and n and m stand each for a positive integer and ($B_7$) polyfunctional monomers based on (meth)acrylate having in the molecule at least one urethane linkage (C) an acidic group-containing monomer based on (meth)acrylate having in the molecule at least one (meth)acryloyloxyl group in an amount, on the weight basis, of from 1 to 50 parts per 100 parts of the sum of monomer (A)+(B); and (D) a trialkylboron or its oxide in an amount, on the weight basis, of from 2 to 100 parts of the sum of monomers (A)+(B)+(C);

wherein, when cured, monofunctional layer (A) and polyfunctional monomer (B) compolymerize to produce a rigid, cross-linked, three-dimensional structure.

2. A curable composition according to claim 1, wherein the acidic group-containing monomer (C) based on (meth)acrylate consists of one or more monomers selected from the group consisting of ($C_1$) aromatic polycarboxylic acids and anhydrides thereof having in the molecule at least one (meth)acryloyloxyl group and ($C_2$) partial esters of phosphoric acid and esters of sulfonic acid each having in the molecule at least one (meth)acryloyloxyl group.

3. A curable composition according to claim 1, wherein the trialkylboron or its oxide (D) consists of one or more compounds selected from the group consisting of triethylboron, tripropylboron, triisopropylboron, tri-n-butylboron, tri-n-amylboron, triisoamylboron, tri-sec-amylboron and oxidation products of them.

4. A curable composition according to claim 1, wherein the proportion of the components (A), (B), (C) and (D) in the composition is in the range of 5–95% by weight for (A), 95–5% by weight for (B) and 1–50 parts by weight for (C), based on the weight of the sum (A)+(B), and 2–100 parts by weight for (D), based on the weight of the sum (A)+(B)+(C).

* * * * *